(12) United States Patent
Kiaei

(10) Patent No.: US 10,791,965 B2
(45) Date of Patent: *Oct. 6, 2020

(54) METHOD AND APPARATUS FOR WIRELESSLY MONITORING REPETITIVE BODILY MOVEMENTS

(71) Applicant: Sayfe Kiaei, Fountain Hills, AZ (US)

(72) Inventor: Sayfe Kiaei, Fountain Hills, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,181

(22) Filed: Apr. 12, 2019

(65) Prior Publication Data

US 2019/0231226 A1 Aug. 1, 2019

Related U.S. Application Data

(63) Continuation of application No. 15/297,943, filed on Oct. 19, 2016, now Pat. No. 10,264,996.

(60) Provisional application No. 62/243,255, filed on Oct. 19, 2015.

(51) Int. Cl.
| | |
|---|---|
| *A61B 5/11* | (2006.01) |
| *A61B 5/113* | (2006.01) |
| *A61B 5/00* | (2006.01) |
| *A61B 5/05* | (2006.01) |
| *A61B 5/024* | (2006.01) |
| *A61B 3/113* | (2006.01) |
| *A61B 5/0205* | (2006.01) |
| *A61B 5/08* | (2006.01) |

(52) U.S. Cl.
CPC ............ *A61B 5/1102* (2013.01); *A61B 3/113* (2013.01); *A61B 5/0205* (2013.01); *A61B 5/0507* (2013.01); *A61B 5/113* (2013.01); *A61B 5/725* (2013.01); *A61B 5/7264* (2013.01); *A61B 5/02444* (2013.01); *A61B 5/0816* (2013.01)

(58) Field of Classification Search
None
See application file for complete search history.

(56) References Cited

U.S. PATENT DOCUMENTS

| 5,809,087 A * | 9/1998 | Ashe ..................... H01Q 3/267 342/165 |
|---|---|---|
| 7,200,266 B2 * | 4/2007 | Ozer .................. G06K 9/00335 382/100 |
| 7,395,181 B2 * | 7/2008 | Foxlin .................. G01C 21/165 128/897 |

(Continued)

*Primary Examiner* — Steven Lim
*Assistant Examiner* — Muhammad Adnan
(74) *Attorney, Agent, or Firm* — Garlick & Markison; Timothy W. Markison; Patricia M. Healy

(57) ABSTRACT

A method for determining a rate of repetitive bodily motion of an individual with negligible contact with the individual begins by one or more computing devices transmitting a signal for reflection off of the individual and receiving a reflected signal. The method continues with one or more computing device applying a frequency estimation algorithm to the baseband signal to produce an estimated spectral density, where the estimated spectral density is in frequency domain and includes at least one frequency component corresponding to the repetitive bodily motion. The method further includes applying a repetitive bodily motion pattern search function to the estimated spectral density to estimate the rate of the repetitive bodily motion of the individual based on the at least one frequency component.

23 Claims, 13 Drawing Sheets

(56) References Cited

U.S. PATENT DOCUMENTS

| | | | | |
|---|---|---|---|---|
| 8,403,865 B2* | 3/2013 | Halperin | A61B 5/113 | 600/584 |
| 8,437,549 B2* | 5/2013 | Iwasaki | G06T 7/215 | 348/208.6 |
| 8,483,806 B2* | 7/2013 | Saint Clair | A61B 5/015 | 382/115 |
| 8,491,492 B2* | 7/2013 | Shinar | A61B 5/0205 | 600/534 |
| 8,977,347 B2* | 3/2015 | Mestha | A61B 5/7235 | 600/473 |
| 8,979,762 B2* | 3/2015 | Ma | A63B 71/0686 | 600/500 |
| 9,131,891 B2* | 9/2015 | Shinar | G16H 40/60 | |
| 9,445,752 B2* | 9/2016 | Jallon | A61B 5/1116 | |
| 9,526,429 B2* | 12/2016 | Heneghan | G16H 50/30 | |
| 9,559,417 B1* | 1/2017 | Schwarzwalder | H04B 7/0456 | |
| 9,671,492 B2* | 6/2017 | Diewald | G01S 7/354 | |
| 9,693,710 B2* | 7/2017 | Mestha | A61B 5/0816 | |
| 10,080,527 B2* | 9/2018 | Golda | A61B 5/04325 | |
| 10,136,853 B2* | 11/2018 | Heinrich | A61B 5/0064 | |
| 10,485,455 B2* | 11/2019 | Maeno | A61B 5/7221 | |
| 2008/0074307 A1* | 3/2008 | Boric-Lubecke | A61B 5/0205 | 342/28 |
| 2010/0026550 A1* | 2/2010 | Rosenbury | A61B 5/02438 | 342/22 |
| 2010/0130873 A1* | 5/2010 | Yuen | A61B 5/0205 | 600/484 |
| 2010/0152600 A1* | 6/2010 | Droitcour | A61B 5/05 | 600/534 |
| 2010/0179438 A1* | 7/2010 | Heneghan | A61B 5/0205 | 600/484 |
| 2010/0198083 A1* | 8/2010 | Lin | A61B 5/05 | 600/484 |
| 2014/0378809 A1* | 12/2014 | Weitnauer | G01S 13/50 | 600/407 |
| 2016/0057565 A1* | 2/2016 | Gold | H04L 67/12 | 455/41.1 |
| 2016/0200276 A1* | 7/2016 | Diewald | G01S 7/354 | 342/28 |
| 2016/0287122 A1* | 10/2016 | Heneghan | A61B 5/04017 | |
| 2017/0042432 A1* | 2/2017 | Adib | A61B 5/08 | |
| 2018/0081030 A1* | 3/2018 | McMahon | A61B 5/0507 | |

* cited by examiner

METHOD AND APPARATUS FOR WIRELESSLY MONITORING REPETITIVE BODILY MOVEMENTS

CROSS REFERENCE TO RELATED PATENTS

This application claims priority pursuant to 35 U.S.C. § 120 as a continuation-in-part of U.S. Utility application Ser. No. 15/297,943, entitled "METHOD AND APPARATUS FOR WIRELESSLY MONITORING REPETITIVE BODILY MOVEMENTS," filed Oct. 19, 2016, which claims priority pursuant to 35 U.S.C. § 119(e) to U.S. Provisional Application No. 62/243,255, entitled "METHOD AND APPARATUS FOR WIRELESSLY MONITORING REPETITIVE BODILY MOVEMENTS," filed Oct. 19, 2015, which are hereby incorporated herein by reference in their entirety and made part of the present U.S. Utility Patent Application for all purposes.

STATEMENT REGARDING FEDERALLY SPONSORED RESEARCH OR DEVELOPMENT—NOT APPLICABLE

INCORPORATION-BY-REFERENCE OF MATERIAL SUBMITTED ON A COMPACT DISC—NOT APPLICABLE

BACKGROUND OF THE INVENTION

Technical Field of the Invention

This invention relates generally to wireless communication and more particularly to a method and apparatus for wirelessly monitoring repetitive bodily movements.

Description of Related Art

Laser (Light Amplification by Stimulated Emission of Radiation) systems are known for their use in wireless data gathering applications. For example, a laser-measuring tool, such as a laser rangefinder, uses a laser beam to determine the distance to and/or from an object. As another example, a laser is used for measurement based on the "time-of-flight" principle, which refers to sending a laser pulse in a narrow beam towards an object, measuring the time taken by the pulse to be reflected off the target, and calculating the distance based on the time. Other laser data gather applications include triangulation, interferometers, phase shift methods, and temperature measurements. Lasers can be used in three-dimensional (3D) object recognition, 3D modeling, and a wide variety of computer vision related fields.

Similarly, radio or microwave frequency signals are known for their use in wireless measurements. For example, radar systems are known object detection systems that use radio or microwaves to determine the range, velocity, or angle of objects. Radar systems use electromagnetic waves to measure distances. Common techniques for measuring distances using electromagnetic waves include time-of-flight, frequency modulation, and phased array method.

Radio and microwave frequency signals are further known for their use in motion detection. A tomographic motion detector uses a mesh system of radio frequency (RF) nodes. Changes in the baseline signal strength between nodes indicate a human presence or motion. This principle is typically implemented using signals in the 2.4 GHz range. A microwave based motion detector operates through the principle of Doppler radar. A continuous wave of microwave radiation is emitted (typically in the range of 915 MHz) and any phase shifts in the reflected microwave due to motion of an object are received as a heterodyne signal at low audio frequencies.

Airport security checkpoints and other security screening locations have implemented full body scanners to wirelessly detect concealed objects under a person's clothing. Whole body scanning is implemented through the use of backscatter X-ray, active millimeter wave, or passive millimeter wave technology. Backscatter X-ray scanners use weak X-rays to detect radiation that reflects from an object to form an image. Images are taken from both sides of the body to create a two-dimensional (2-D) image of the person and anything else on that person's body. Active millimeter wave scanners direct millimeter wave energy at the person and interpret the reflected energy. Because clothing and many other materials are translucent to extremely high frequency bands (EHF) such as the 24-30 GHz band emitted by millimeter-wave scanners, the wave energy reflected back from the body or other objects on the body is used to construct a 3D image, which can be displayed for analysis. In contrast, passive millimeter wave scanners create images using ambient radiation and radiation emitted from the human body or objects.

Bluetooth is a known wireless technology for exchanging data over short distances from fixed and/or mobile devices and building personal area networks (PANs). Bluetooth technology uses short wavelength, ultra high frequency (UHF) radio waves in the industrial, scientific, and medical (ISM) radio band from 2.4 to 2.48 GHz to establish wireless connections between devices.

Currently, "wireless" heart rate monitors include a sensor that makes contact with the body (e.g., a sensor attached to the wrist, across the chest, etc.) that wirelessly communicates with another device (e.g., a smart phone, watch, etc.). As such, wireless heart rate monitors require contact with the human body to sense the appropriate data.

BRIEF DESCRIPTION OF THE SEVERAL VIEWS OF THE DRAWING(S)

DETAILED DESCRIPTION OF THE INVENTION

Figure 1:
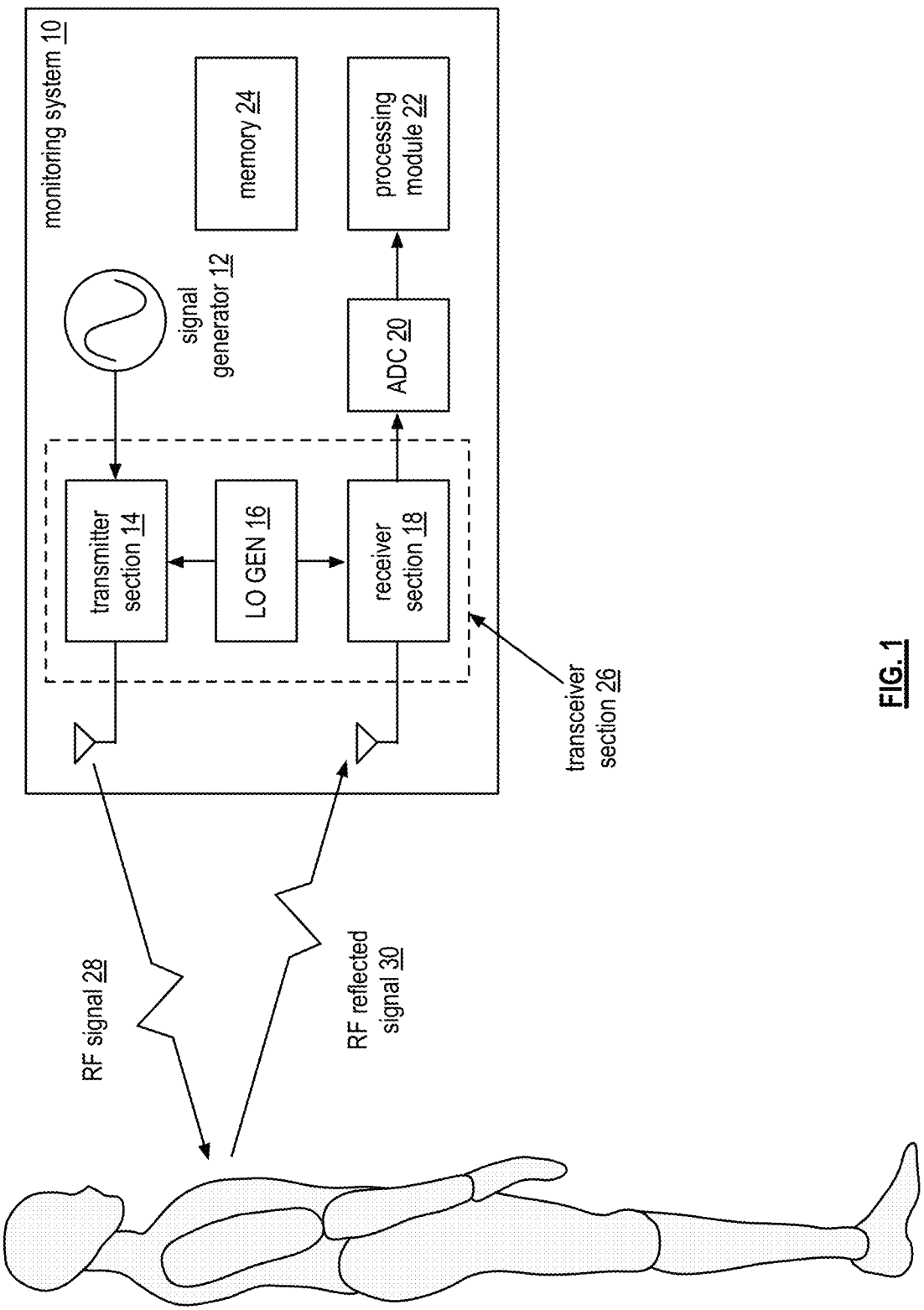
FIG. 1 is a schematic block diagram of an embodiment of a wireless monitoring repetitive bodily movement system in accordance with the present invention.

FIG. 1 is a schematic block diagram of an embodiment of a wireless monitoring repetitive bodily movement system 10 ("monitoring system"), which may be implemented via one or more computing devices. The monitoring system 10 includes a signal generator 12, a transceiver section 26, an analog to digital converter (ADC) 20, memory 24, and a processing module 22. The transceiver section 26 includes a transmitter section 14, a local oscillation generator (LO GEN) 16, a receiver section 18, and antennas.

A computing device may be a portable computing device and/or a fixed computing device. A portable computing device may be a social networking device, a gaming device, a cell phone, a smart phone, a personal digital assistant, a digital music player, a digital video player, a laptop computer, a handheld computer, a tablet, a video game controller, and/or any other portable device that includes a computing core (e.g., includes one or more of main memory, a processing module, a memory controller, input/output controller, external memory interface, and peripheral device controller). A fixed computing device may be a personal computer (PC), a computer server, a cable set-top box, a satellite receiver, a television set, a printer, a fax machine, home entertainment equipment, a video game console, and/or any type of home or office computing equipment that includes a computing core.

In an example of operation, the signal generator 12 generates a continuous wave reference signal (e.g., a 30 kHz sinusoidal signal) for transmission. The transmitter section 14 up-converts the continuous wave reference signal to a radio frequency signal (e.g., a 2.4 GHz signal) and transmits the signal (e.g., radio frequency (RF) signal 28) for reflection off of an individual. The individual could include a human, animal, reptile, or any being capable of producing a repetitive bodily motion. The repetitive bodily motion may include heartbeat, respiration, eye movement, spasms, ticks, or any other repetitive bodily movement.

The receiver section 18 receives a reflected signal 30, which is corresponds to the transmitted RF signal 28 being reflected and/or refracted off of the individual. The reflected signal 30 includes one or more of the transmitted signal 28, a clutter signal component (e.g., reflection of the transmit signal 28 off of objects other than the individual), a multipath signal component (e.g., non-direct path reflections of the transmitted signal off of the individual), a noise signal component, and a Doppler shifted version of a repetitive bodily motion of the individual (e.g., the desired signal). For example, the chest wall and the heart wall oscillate and have zero net velocity. The Doppler shift due to the heartbeat and respiration movement of the chest can be expressed by phase modulation of the reflected signal 30. As such, the reflected signal 30 includes Doppler shifted version of the repetitive bodily motion (e.g., heartbeat and/or respiration movements of the chest).

The receiver section 18 down-converts the reflected signal 30 to an intermediate frequency (IF) (e.g., 30 KHz). The ADC 20 converts the analog IF signal into a digital IF signal. As will be described in greater detail with reference to one or more of FIGS. 5-14, the processing module 22 down converts the IF signal to a baseband signal (e.g., removes the 30 KHz signal component). The processing module 22 processes the baseband signal to remove or substantially reduce the clutter signal component, the multipath signal component, and the noise signal component of the baseband signal, leaving the desired Doppler shift signal component(s) of the repetitive bodily motion.

In order to isolate the Doppler shifted signal components of the signal, the processing module 22 applies a frequency estimation algorithm to the baseband signal to produce an estimated spectral density. The processing module 22 then applies a repetitive bodily motion pattern search function to the estimated spectral density to detect the Doppler shifts and estimate the rate of the repetitive bodily motion of the individual with negligible contact with the individual. Knowing that the Doppler shifted version of the repetitive bodily motion (e.g., the heart rate and/or respiration) are within certain frequency ranges help fine tune the repetitive bodily motion pattern search function. The monitoring system 10 is further operable to output the rate of the detected repetitive bodily motion of the individual for display and/or further analysis.

Figure 2:
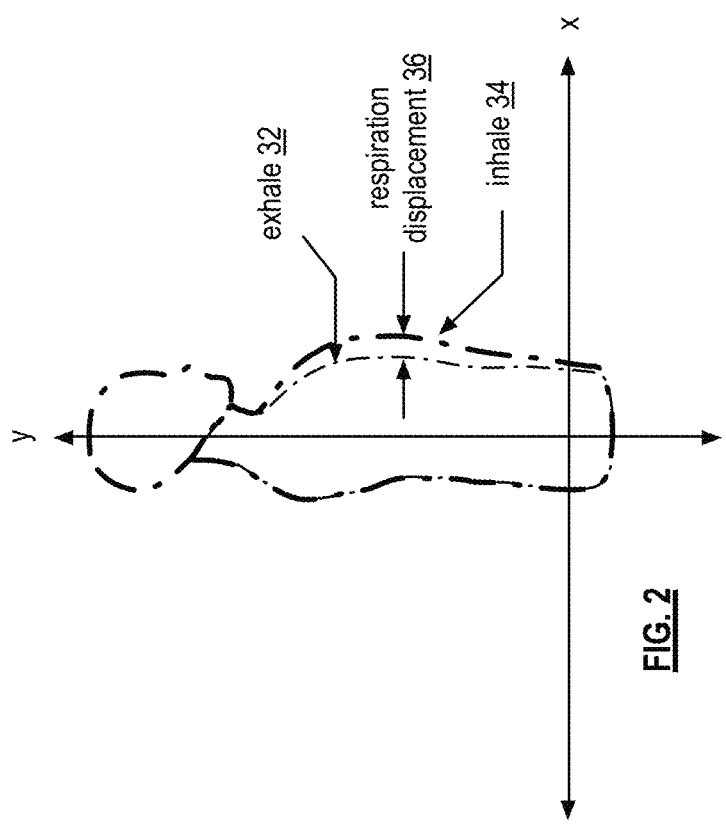
FIGS. 2 and 3 are diagrams of an example of human respiration and heart rate.
Figure 3:
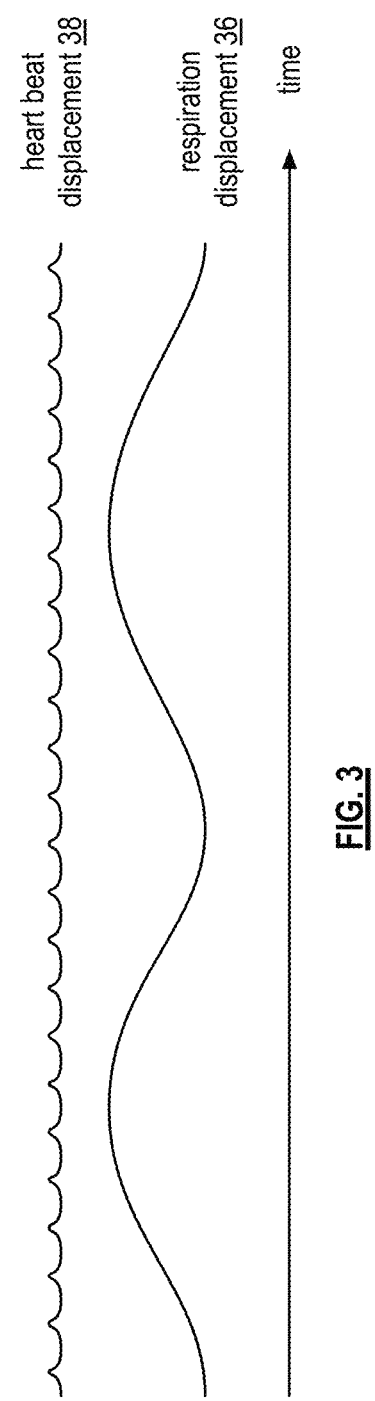

FIGS. 2 and 3 are diagrams of an example of the repetitive bodily motions of human respiration and heart rate. FIG. 2 depicts an example of chest displacement caused during respiration. When exhaling 32, the chest falls and upon inhaling 34, the chest rises. This respiration displacement 36 may be a few centimeters or more. Similarly, the movement of a heartbeat causes a small displacement of the chest of a few millimeters or more. FIG. 3 depicts heartbeat displacement 38 and respiration displacement 36 as displacement over time. Heartbeat displacement 38 has a higher frequency but smaller amplitude in comparison to the respiration displacement 36. Known properties of these signals can aid in the detection and tuning of the Doppler shifted versions of repetitive bodily motion present in the reflected signal.

Figure 4:
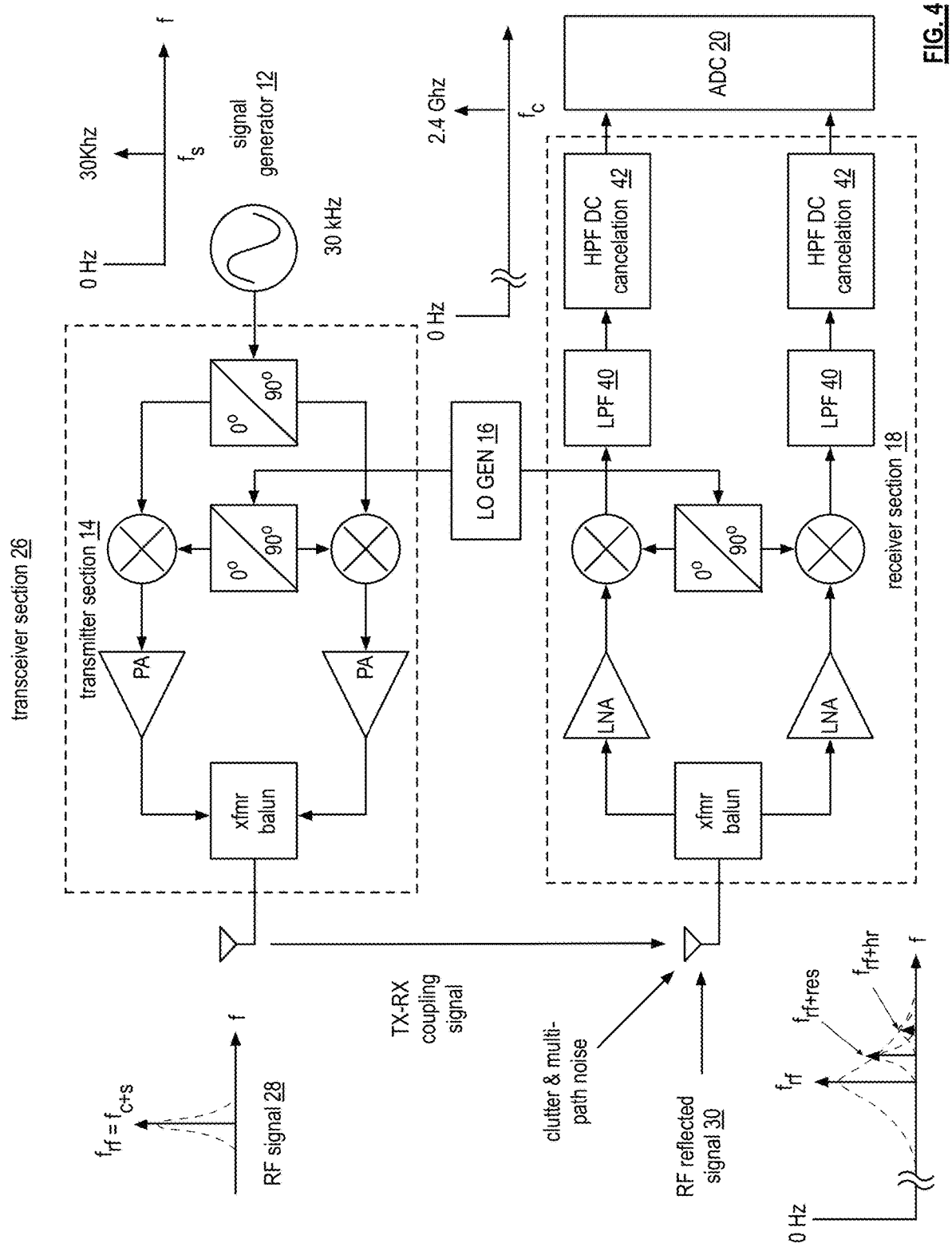
FIG. 4 is a schematic block diagram of an embodiment of a transceiver section of the wireless monitoring repetitive bodily movement system in accordance with the present invention.

FIG. 4 is a schematic block diagram of an embodiment of the transceiver section 26 of the monitoring system 10 that includes the transmitter section 14 and the receiver section 18. The transmitter section 14 includes IQ phase shift modules)(0°,90°, mixers, power amplifiers (PA), a transformer balun (xfmr balun), and an antenna. The receiver section 18 includes an antenna, a transformer balun, low noise amplifiers, mixers, an IQ phase shift module, low pass filters (LPF) 40, and high pass filter DC cancelation modules 42.

In an example of operation, the signal generator 12 generates a continuous wave reference signal (e.g., a 30 KHz continuous wave sinusoidal reference signal). An IQ phase shift module generates an in-phase reference signal (0° phase shift) and a quadrature reference signal (90° phase shift). The local oscillator generator (LO GEN) 16 generates a transmitter local oscillation (e.g., 2.4 GHz) and a receive local oscillation (e.g., 2.4 GHz). Note that the transmit and receive location oscillations may be separate signals or the same signal.

A second IQ phase shift module generates an in-phase local oscillation signal (0° phase shift) and a quadrature local oscillation signal (90° phase shift) from the transmit local oscillation. A first mixer mixes in-phase reference signal (e.g., sin $\Phi(t)$) with the in-phase local oscillation (e.g., sin $\omega_{LO}(t)$) to produce a first up-converted signal component (e.g., ½ *cos($\omega_{LO}(t)-\Phi(t)$)−½*cos($\omega_{LO}(t)+\Phi(t)$)). A second mixer mixes the quadrature reference signal (e.g., cos $\Phi(t)$) with the quadrature local oscillation signal (e.g., cos $\omega_{LO}(t)$) to produce a second up-converted signal component (e.g., ½ *cos($\omega_{LO}(t)-\Phi(t)$)+½ *cos($\omega_{LO}(t)+\Phi(t)$)).

The power amplifiers amplify the first and second up-converted signals, which are summed via the transformer balun to produce the transmit RF signal 28 (e.g., cos $\omega_{RF}(t)$=cos($\omega_{LO}(t)+\Phi(t)$)). Alternatively, the first and second up-converted may be summed prior to amplification by a power amplifier. Note that one or more RF bandpass filters may be included in prior to and/or after the power amplifiers.

The resulting RF signal 28 is transmitted via the antenna. The antenna may be a single omnidirectional antenna, a single directional antenna, and/or two or more diversity antennas. The antenna may further include beamforming to focus the transmitted RF signal.

The radio frequency signal 28 is reflected off of an individual and received by the antenna of the receiver section 18 as the reflected signal 30. The reflected signal 30 includes a Doppler shifted version of the repetitive bodily motion, a clutter signal component (e.g., reflection of the RF signal 28 off of other objects), a multipath signal component (e.g., indirect signal paths of the RF signal reflecting off of the individual), a transmit-receive coupled signal component (e.g., reception of the RF signal 28 via cross coupling within the transceiver), and a noise component (e.g., phase noise of the LO GEN).

The clutter, multipath, transmit-receive coupling, and the noise signal components are in-band interferers with the desired Doppler shifted version of the repetitive bodily motion signal component. In particular, the LO GEN 16 does not generate a clean sinusoidal signal but rather it creates one with a time varying random phase noise, $\theta(t)$. Hence the practical transmit local oscillation is, s(t)=sin (2$\pi f_c t + \theta(t)$) (where $f_c$ is the frequency, e.g., 2.4 GHz). Therefore, the spectrum of s(t) is not a delta function as in the ideal case, but has an extended skirt due to phase noise. When this signal under goes a Doppler shift due to a repetitive bodily motion, the complete spectra of the signal is shifted as illustrated in the bottom left of FIG. 4. The Doppler shift signal components (e.g., $f_{rf\text{-}res}$ and $f_{rf\text{-}hr}$, where "res" corresponds to respiration and "hr" corresponds to heart rate) are small and fall in the region of this skirt. The clutter, multipath, transmit-receive coupling signal components further contribute to the skirt.

In an example of operation, the receiver section 18 receives the reflected signal 30. The transformer balun converts the single ended signal reflected signal 30 into a differentiated signal (e.g., an in-phase reflected signal and a quadrature reflected signal). The in-phase reflected signal and a quadrature reflected signal are each amplified by low noise amplifiers (LNA). A first mixer mixes the amplified in-phase reflected signal (e.g., sin $\omega_{RF}(t)$) with an in-phase receive local oscillation (e.g., sin $\omega_{LO}(t)$) from LO GEN 16 and a second mixer mixes the amplified quadrature reflected signal (e.g., cos $\omega_{RF}(t)$) with a quadrature receive local oscillation (e.g., cos $\omega_{LO}(t)$).

Low pass filters 40 filter the mixed in-phase signal (e.g., ½*cos($\omega_{RF}(t)-\omega_{LO}(t)$)−½*cos($\omega_{RF}(t)+\omega_{LO}(t)$)) and mixed quadrature signal (e.g., ½*cos($\omega_{RF}(t)-\omega_{LO}(t)$)−½*cos($\omega_{RF}(t)+\omega_{LO}(t)$)) to produce a down-converted in-phase intermediate frequency (IF) signal (e.g., ½*cos($\omega_{RF}(t)-\omega_{LO}(t)$)=½ *cos($\omega_{RF}(t)$)), where $\omega_{RF}(t)$ has a frequency corresponding to the frequency of the reference signal $\Phi(t)$ and a down-converted quadrature IF signal (e.g., ½*cos($\omega_{RF}(t)-\omega_{LO}(t)$)=½*cos($\omega_{RF}(t)$)). The high pass filter DC cancelation filters 42 filter the down-converted in-phase IF signal and the down-converted quadrature IF signal to substantially attenuate signal components below the intermediate frequency (e.g., 30 KHz). The ADC 20 converts the down-converted in-phase (I) and quadrature (Q) IF signals into digital I and Q IF signals.

Figure 5:
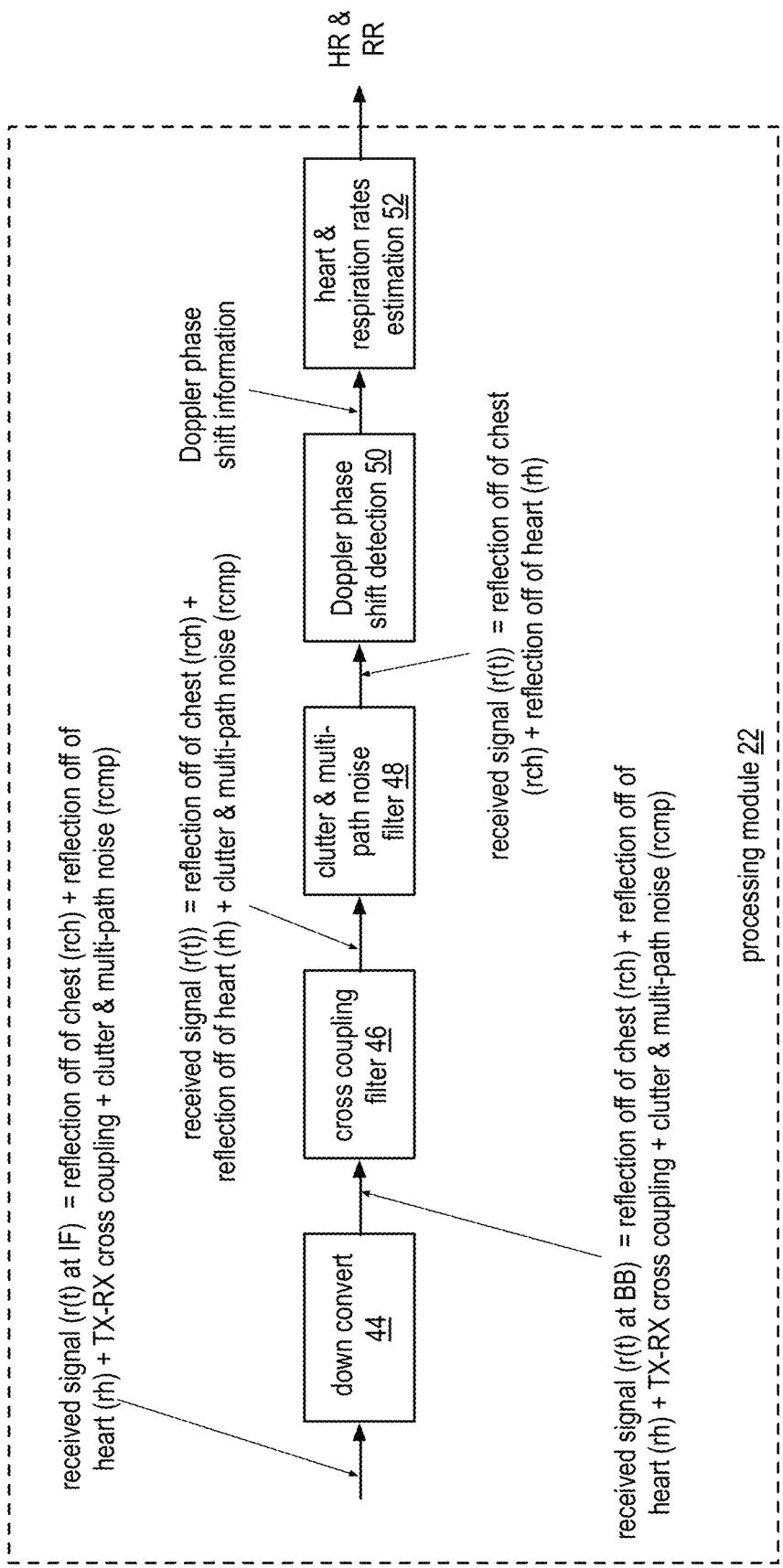
FIG. 5 is a schematic block diagram of an embodiment of a processing module of the wireless monitoring repetitive bodily movement system in accordance with the present invention.

FIG. 5 is a schematic block diagram of an embodiment of the processing module 22 of the monitoring system 10. The processing module 22 is configured to include a down convert module 44, a cross coupling filter 46, a clutter and multi-path noise filter 48, a Doppler phase shift detection module 50, and a repetitive bodily movement rate estimation module 52 (e.g., shown here as a heart and respiration rate estimation module).

In an example of operation, the processing module 22 receives the digital I and Q IF signals (hereinafter referred to as IF signal) from the ADC 20. The IF signal includes an IF carrier frequency component, the desired Doppler shifted version of the repetitive bodily motions signal component (e.g., reflection off chest (rch) and reflection off heart (rh)), the TX-RX cross coupling signal component, and clutter and multipath noise signal component (rcmp). The down convert module 44 down converts the IF signal to a baseband signal by removing the IF carrier frequency component. The cross coupling filter 46 substantially removes the TX-RX cross coupling signal component from the baseband signal. The clutter and multipath noise filter 48 removes the clutter and noise signal components from the baseband signal. The Doppler phase shift detection module 50 searches the baseband signal for Doppler shifted version of repetitive bodily motions signal components. The repetitive bodily movement rate estimation module 52 interprets the Doppler phase shift signal components to estimate the repetitive bodily movement (e.g., the heart and respiration rate estimation module). For example, based on an expected range of frequencies for heart rate (e.g., 60-80 beats per minute) and respiration (e.g., 16-20 breathes per minute), the repetitive bodily movement rate estimation module 52 identifies the heart rate and the respiration rate from the Doppler phase shift information corresponding to those frequencies.

Figure 6:
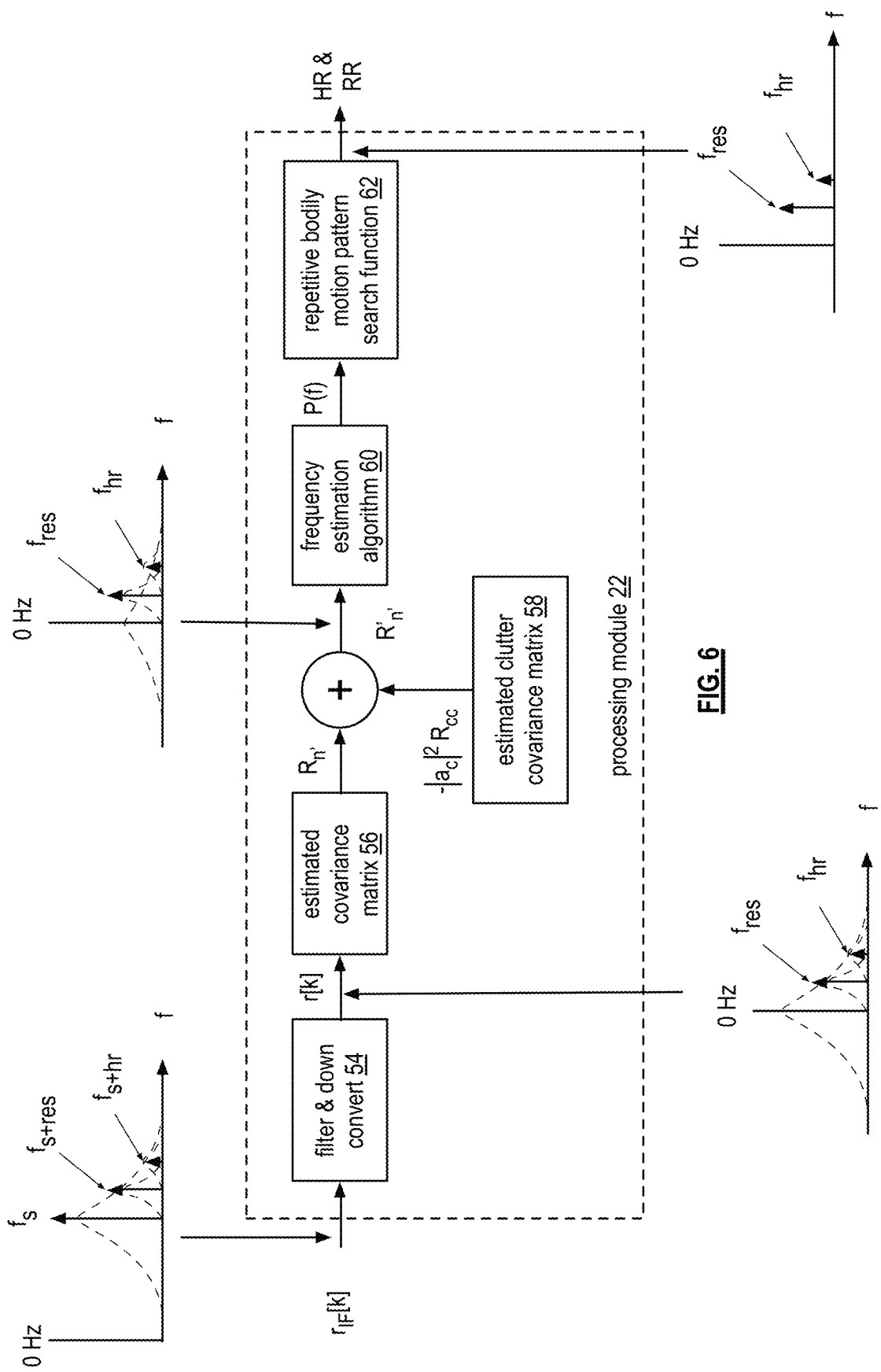
FIG. 6 is a schematic block diagram of another embodiment of a processing module of the wireless monitoring repetitive bodily movement system in accordance with the present invention.

FIG. 6 is a schematic block diagram of another embodiment of the processing module 22 of the monitoring system 10. The processing module 22 is implemented to include a filter and down convert module 54, an estimate covariance matrix module 56, an estimate clutter covariance matrix module 58, an adder, a frequency estimation algorithm module 60, and a repetitive bodily motion pattern search function module 62.

In an example of operation, the filter and down convert module 54 receives the sampled, down converted IF signal (e.g., $r_{IF}[k]$) from the transceiver section. The filter and down convert module 54 down-converts the sampled IF signal to a baseband signal. For example, the module 54 low pass filters the IF signal to a stop frequency (e.g., of 50 Hz) and then down samples the filtered signal such that the new sampling frequency is 50 Hz. This process removes the intermediate frequency (e.g., 30 KHz) from the signal and shifts the signal components closer to 0 Hz to create a filtered and down-sampled baseband signal at DC (e.g., r[k]).

In order to remove the TX-RX cross coupling and cancel the clutter and multi path noise from the signal, the estimate covariance matrix module 56 estimates the signal's covariance matrix over a window of samples and averages it over multiple overlapping windows. To estimate the covariance matrix of the signal, the estimate covariance matrix module 56 captures the transmitted signal through shorting the transmit and receive paths to estimate the covariance of the transmitted signal. The transmitted signal and the noise (e.g., Additive White Gaussian Noise (AWGN)) components of the received signal are assumed to be random, independent variables. Next, K number of samples of the received signal is windowed. The covariance matrix can then be calculated (as a function of the random variables, the covariance matrix of the transmitted signal, the variance of the AWGN, and the multi path components and their respective Doppler shifts) over this window. The covariance matrix of the baseband signal (e.g., $R_n$) is averaged by sliding the window over the entire duration of the captured signal.

Next, the estimate clutter covariance matrix 58 estimates the baseband signal's clutter covariance matrix. The estimate clutter covariance matrix 58 first records a received signal without an individual in front of the monitoring system 10 to estimate the clutter multi path reflection due to ambiance (e.g., a loop back measurement). Then the estimate clutter covariance matrix 58 calculates the covariance matrix of the clutter signal as a function of the random variables, the covariance of the transmitted signal, the variance of the AWGN, and the multi path components and their respective Doppler shifts. The clutter covariance matrix (e.g., Rcc) is then scaled by the ratio of the TX/RX coupling power (e.g., $|\alpha_c|^2$) determined during the loop back measurement. The baseband covariance matrix is then subtracted by the clutter covariance matrix to produce a resultant matrix (e.g., $R'_n$). By subtracting the clutter covariance matrix from the covariance matrix after scaling it with the appropriate scalar, the clutter can be canceled and the SNR (signal to noise ratio) of repetitive bodily motion signal (e.g., heart rate signal, respiration signal, etc.) can be increased.

With the clutter from the baseband signal now canceled (i.e., significantly attenuated to render the clutter signal component insignificant), the frequency estimation algorithm module 60 applies a frequency estimation algorithm to the resultant matrix ($R'_n$) to produce an estimated spectral density (P(f)) in order to accurately estimate closely spaced signals in frequency domain. A frequency estimation algorithm such as Multiple Signal Classification (MUSIC) is able to estimate the pseudo spectrum of a signal or a correlation matrix using an eigen space analysis method. For instance, the MUSIC algorithm detects frequencies in a signal by performing an eigen decomposition on the resultant matrix of the baseband signal. From the eigen decomposition of the baseband resultant matrix, the eigen vectors associated with the N maximum eigenvalues are used to define the signal subspace and other eigenvectors are used to define the noise subspace. From the orthogonality of the signal and noise subspaces, the peaks can be found in the estimator function 60. These peaks represent the estimated spectral density (P(f)) of the signal.

The estimated spectral density (P(f)) is then used by the repetitive bodily motion pattern search function module 62 to identify components that are indicative of repetitive bodily motion. For example, a heartbeat and respiration search function is applied to the estimated spectral density to search for and determine principal components of heartbeat and respiration. Then the heart rate and a respiration rate can be estimated from the determined principal components. As another example, an eye movement search function can be applied to the estimated spectral density to determine principal components of eye movement, wherein the eye movement corresponds to the repetitive bodily motion. Based on the determined principal components of eye movement, the eye movement rate can be estimated.

Figure 7:
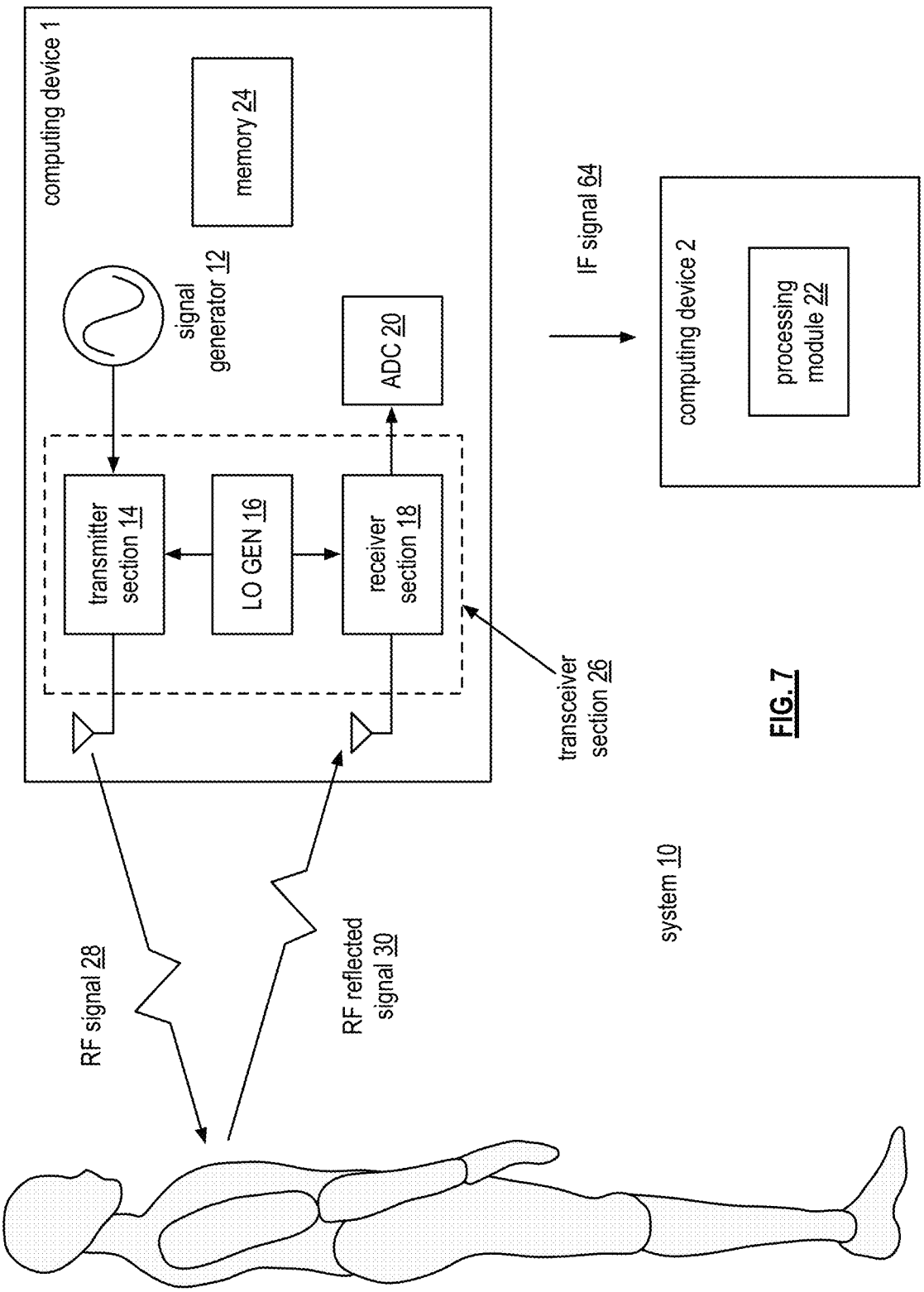
FIG. 7 is a schematic block diagram of an embodiment of a wireless monitoring repetitive bodily movement system in accordance with the present invention.

FIG. 7 is a schematic block diagram of another embodiment of the wireless monitoring repetitive bodily movement system 10. The wireless monitoring repetitive bodily movement system 10 includes computing device 1 and computing device 2. Computing device 1 includes a signal generator 12, a transceiver section 26, an analog to digital converter (ADC) 20, and memory 24. The transceiver section 26 includes a transmitter section 14, a local oscillation generator (LO GEN) 16, a receiver section 18, and antennas. Computing device 2 includes processing module 22.

In an example of operation, the transmitting the signal for reflection off of the individual is performed by a first computing device (e.g., computing device 1) of one or more computing devices. The signal generator 12 generates a continuous wave reference signal (e.g., a 30 kHz sinusoidal signal) for transmission. The transmitter section 14 up-converts the continuous wave reference signal to a radio frequency signal and transmits the signal (e.g., radio frequency (RF) signal 28) for reflection off of the individual.

The receiver section 18 receives the reflected signal 30, wherein the reflected signal 30 includes one or more of the transmitted signal, a clutter signal component, a multipath signal component, a noise component, and a Doppler shifted version of a repetitive bodily motion of the individual. The repetitive bodily motion may include heartbeat, respiration, eye movement, spasms, ticks, or any other repetitive bodily movement. For example, the reflected signal could contain Doppler shifted versions of the heartbeat and respiration movement of the chest. The receiver section 18 and the ADC 20 sample and down-convert the reflected signal 30 to an IF signal 64.

Computing device 2 receives the baseband signal 64 via a wired and/or wireless connection to computing device 1. The processing module 22 applies the frequency estimation algorithm to the baseband signal to produce the estimated spectral density. The processing module 22 then applies a repetitive bodily motion pattern search function to the estimated spectral density to estimate the rate of the repetitive bodily motion of the individual with negligible contact with the individual. Knowing that the Doppler shifted version of the repetitive bodily motion (e.g., the heart rate and respiration) are within certain frequency ranges help fine tune the repetitive bodily motion pattern search function.

Figure 8:
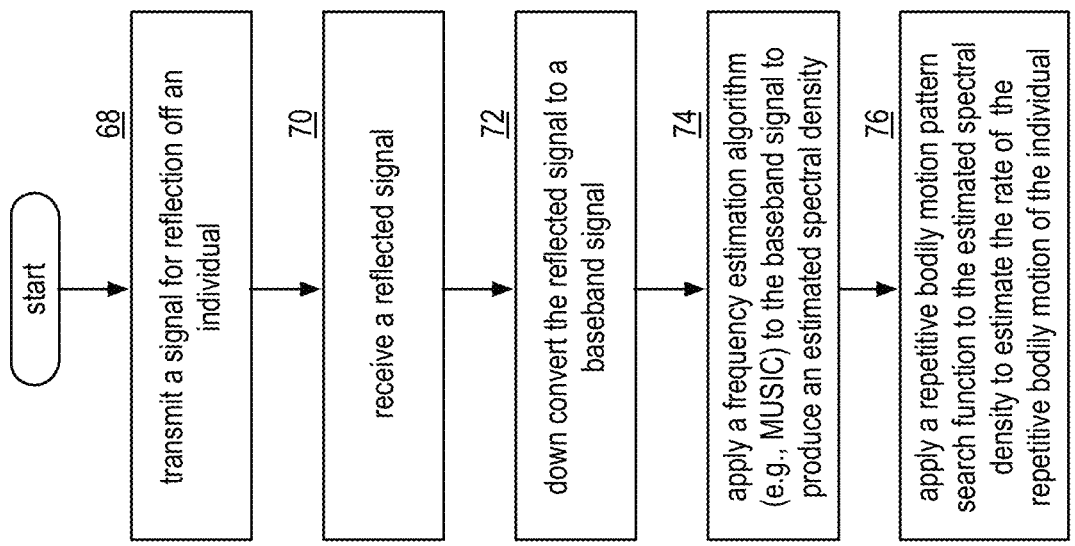
FIG. 8 is a flowchart illustrating an example of determining a rate of repetitive bodily motion in accordance with the present invention.

FIG. 8 is a flowchart illustrating an example of determining a rate of repetitive bodily motion. The method for determining a rate of repetitive bodily motion of an individual with negligible contact with the individual, is executable by one or more computing devices and begins with step 68 where a signal is transmitted for reflection off of an individual. An individual may include a human, animal, reptile, or any being capable of producing a repetitive bodily motion. The repetitive bodily motion includes at least one of heartbeat, respiration, eye movement, spasms, and ticks. Transmitting the signal includes the steps of generating a continuous wave reference signal, up-converting the continuous wave reference signal to a radio frequency signal, and transmitting the radio frequency signal as the signal for reflection off the individual.

The method continues with step 70 where a reflected signal is received. The reflected signal includes one or more signal components including the transmitted signal, a clutter signal, a multipath signal, a noise component, and a Doppler shifted version of the repetitive bodily motion. The reflected signal may be a reflection and/or a refraction of the transmitted off of the individual.

The method continues with step 72 where the received signal is down converted to a baseband signal. The received signal is first down-converted to an IF signal at an intermediate frequency (e.g., 30 KHz) and over-sampled. The down-converted, oversampled signal is then further processed to remove the intermediate frequency thereby producing a baseband signal.

The method continues with step 74 where a frequency estimation algorithm (e.g., MUSIC) is applied to the baseband signal to produce an estimated spectral density. In order to apply the frequency estimation algorithm, the baseband signal is further processed to remove (i.e., substantially attenuate) the clutter signal, multipath signal, and noise component from the baseband signal. These components are separated and removed from the signal so that the components that are indicative of the repetitive bodily movement (e.g., the Doppler shifted version of the repetitive bodily motion) may be isolated. Once these components are isolated, the frequency estimation algorithm (e.g., MUSIC) is applied to the baseband signal to produce the estimated spectral density. An example of applying the frequency estimation algorithm is further discussed with reference to FIG. 9.

The method continues with step 76 where a repetitive bodily motion pattern search function is applied to the estimated spectral density to estimate the rate of the repetitive bodily motion of the individual. An example of applying the repetitive bodily motion pattern search function is further discussed with reference to FIG. 10. The rate of the repetitive bodily motion can then be outputted for display and/or further analysis.

Figure 9:
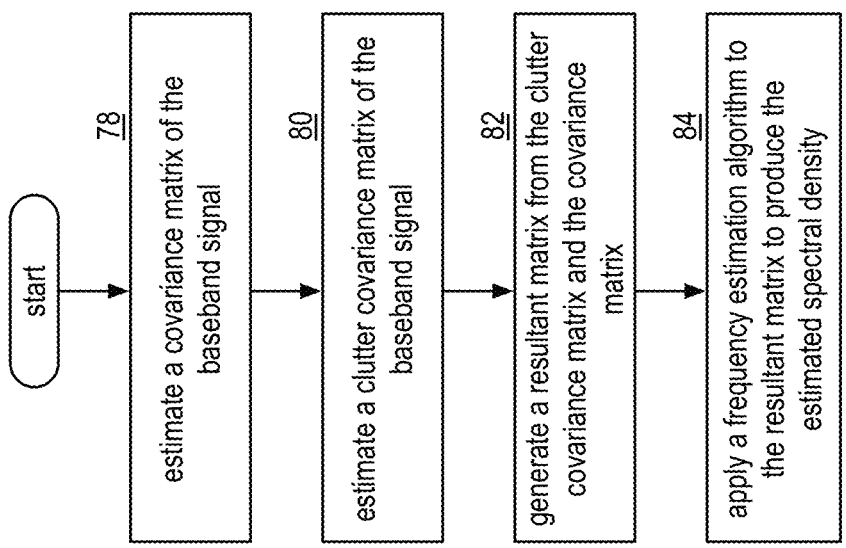
FIG. 9 is a flowchart illustrating an example of applying a frequency estimation algorithm in accordance with the present invention.

FIG. 9 is a flowchart illustrating an example of applying a frequency estimation algorithm. The method begins with step 78 where the covariance matrix of the baseband signal is estimated. In order to remove the TX-RX cross coupling and cancel the clutter and multi path noise from the baseband signal so that the frequency estimation algorithm can be applied, the baseband signal's covariance matrix is estimated over a window of samples and averaged over multiple overlapping windows. To estimate the covariance matrix of the signal, the transmitted signal is captured by shorting the transmit and receive paths to estimate the covariance of the transmitted signal. The transmitted signal and the noise (e.g., Additive White Gaussian Noise (AWGN)) components of the baseband signal are assumed to be random, independent variables. Next, K number of samples of the received signal is windowed. The covariance matrix can then be calculated (as a function of the random variables, the covariance matrix of the transmitted signal, the variance of the AWGN, and the multi path components and their respective Doppler shifts) over this window. The covariance matrix of the baseband signal is averaged by sliding the window over the entire duration of the captured signal.

The method continues with step 80 where the clutter covariance matrix of the baseband signal is estimated. The clutter covariance matrix is estimated by first recording the received signal without an individual in front of the device to estimate the clutter multi path reflection due to ambiance (e.g., a loop back measurement). The clutter signal can then be estimated as a function of the random variables, the covariance of the transmitted signal, the variance of the AWGN, and the multi path components and their respective Doppler shifts. The clutter covariance matrix is then scaled by the ratio of the TX/RX coupling power determined during the loop back measurement.

The method continues with step 82 where the resultant matrix is generated from the clutter covariance matrix and the covariance matrix of the baseband signal. By subtracting the clutter covariance matrix from the covariance matrix after scaling it with the appropriate scalar, the clutter can be canceled and the SNR of repetitive bodily motion signal (e.g., heart rate signal) can be increased.

The method continues with step 84 where the frequency estimation algorithm is applied to the resultant matrix to produce the estimated spectral density. With the clutter signal, multipath signal, and noise components from the baseband signal now canceled, the frequency estimation algorithm such as Multiple Signal Classification (MUSIC) is applied. The frequency estimation algorithm such as MUSIC is able to estimate the pseudospectrum of a signal or a correlation matrix using an eigenspace analysis method. For instance, the MUSIC algorithm detects frequencies in the baseband signal by performing an eigen decomposition on the resultant matrix of the baseband signal. From the eigen decomposition of the baseband resultant matrix, the eigenvectors associated with the N maximum eigenvalues are used to define the signal subspace and other eigenvectors are used to define the noise subspace. From the orthogonality of the signal and noise subspaces, the peaks can be found in the estimator function. These peaks represent the estimated spectral density of the signal.

Figure 10:
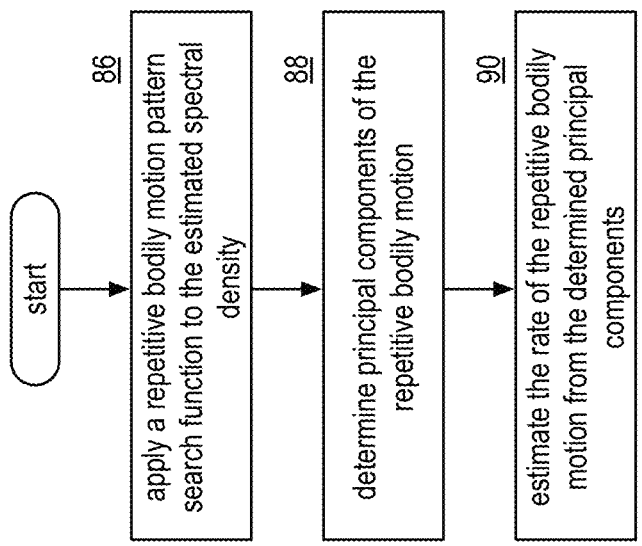
FIG. 10 is a flowchart illustrating an example of applying a repetitive bodily motion pattern search function in accordance with the present invention.
Figure 11:
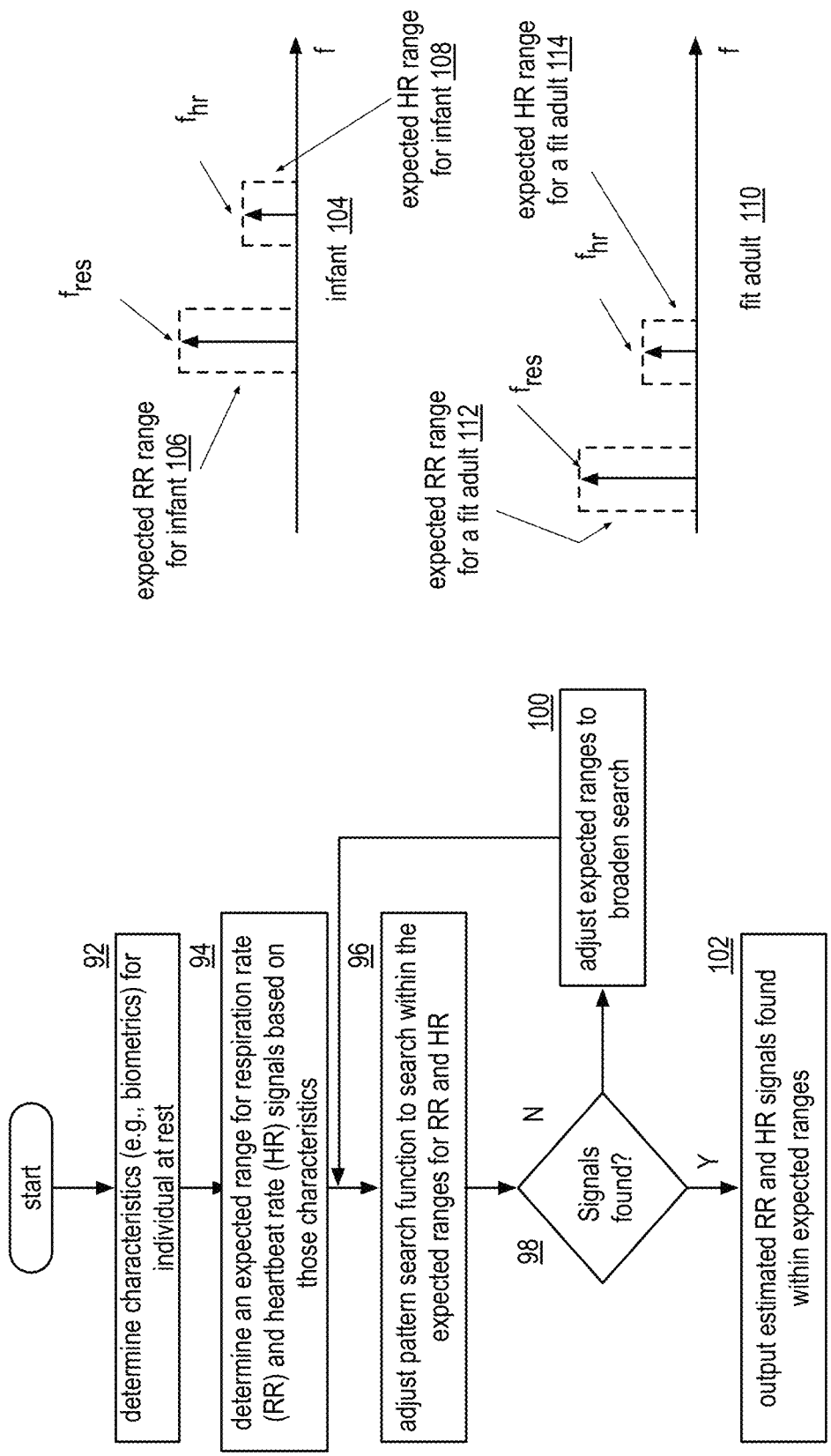
FIG. 11A is a flowchart illustrating another example of applying the repetitive bodily motion pattern search function in accordance with the present invention.
FIG. 11B is a diagram of an example of human respiration and heart rate frequencies.

FIG. 10 is a flowchart illustrating an example of applying a repetitive bodily motion pattern search function. The method begins with step 86 where the repetitive bodily motion pattern search function is applied to the estimated spectral density of the baseband signal. As an example, a heartbeat and respiration search function is applied to the estimated spectral density. As another example, an eye movement search function can be applied to the estimated spectral density.

The method continues with step 88 where principal components of the repetitive bodily motion are determined. For example, the heartbeat and respiration search function is applied to the estimated spectral density to search for and determine principal components of heartbeat and respiration. As another example, the eye movement search function can be applied to the estimated spectral density to determine principal components of eye movement, wherein the eye movement corresponds to the repetitive bodily motion.

The method continues with step 90 where the rate of the repetitive bodily motion is estimated based on the determined principal components. For example, the determined principal components of heartbeat and respiration are used to estimate heart rate and respiration rate. As another example, the determined principal components of eye movement are used to estimate the rate of eye movement.

FIG. 11A is a flowchart illustrating another example of applying the repetitive bodily motion pattern search function. The method begins with set step 92 where the characteristics (e.g., biometrics) of an individual are determined at rest. Biometrics of the individual may include age, sex, size, and physical condition (e.g., athlete, sedentary lifestyle, moderately active lifestyle, etc.).

The method continues with step 94 where an expected range for respiration rate (RR) and heartbeat rate (HR) signals are determined based on those characteristics. Depending on the biometrics of the individual, the expected range of the respiration rate and heartbeat rate can differ. For example, a male athlete between the ages of 18-25 should have an average resting heart rate of about 49-55 beats per minute (BPM) whereas a male in the same age range with average physical condition should have an average resting heart rate of about 70-73 BPM. A female athlete between the ages of 18-25 should have an average resting heart rate of about 54-60 BPM whereas a female in the same age range with average physical condition should have an average resting heart rate of about 74-78 BPM. Further, a male athlete over the age of 65 should have an average resting heart rate of about 50-55 BPM and a female athlete over the age of 65 should have an average resting heart rate of about 54-59 BPM.

In general, well-conditioned athletes will typically have a resting heart rate ranging from 40-60 BPM. Children over the age of 10 and adults will typically have a resting heart rate ranging from 60-100 BPM. Children between the ages of 1-10 will typically have a resting heart rate ranging from 70-130 BPM. Infants between the ages of 6-12 months old will typically have a resting heart rate ranging from 100-160 BPM. Infants between the ages of 3-6 months old will typically have a resting heart rate ranging from 90-120 BPM and newborns (0-3 months) will typically have a resting heart rate ranging from 100-150 BPM.

Likewise, respiration rates differ based on age, sex, and physical condition. Age plays a primary role in differing respiration rates. For example, newborns between the ages of 0-6 weeks have a respiration rate of 30-60 breaths per min. Infants at 6 months old have a respiration rate of 25-40 breaths per min. Children at 3 years old have a respiration rate of 20-30 breaths per min. Children at 6 years old have a respiration rate of 18-25 breaths per min. Children at 10 years old have a respiration rate of 12-15 breaths per min. Adults generally have a respiration rate of 16-20 breaths per min. Elderly persons over the age of 65 typically have a respiration rate of 12-28 breaths per minute. Elderly persons over the age of 80 typically have a respiration rate of 10-30 breaths per minute.

The method continues with step 96 where the pattern search function is adjusted to search within the expected ranges for respiration rate and heartbeat rate. The parameters of the frequency estimation algorithm may also be adjusted depending on the expected range of frequencies. For instance, if the individual is an adult male with average physical condition his heart rate is most likely between 70-73 beats per minute and his respiration rate is somewhere between 16-20 breaths per min. The pattern search function would be adjusted to search the baseband signal's estimated spectral density for frequencies representative of those specified ranges.

The method continues with step 98 where it is determined whether signals are found within the expected range. If no signals are located within the expected ranges, the method continues with step 100 where the expected ranges are adjusted to broaden the search. For instance, even though the individual being measured in this example (the adult male with average physical condition) has an average heart rate of 70-73 beats per minute and an average respiration rate between 16-20 breaths per min, other factors such as stress, injury, anxiety, diet, and fatigue can put actual heartbeat and respiration rates outside of the expected range. For instance, if the individual is slightly nervous his heart rate may in fact be at 80 beats per minutes instead of within the expected range of 70-73 beats per min. When the signal is not found in this expected range, the search function will adjust to search outside of the expected range until a signal is found.

For example, at step 100, the expected range (e.g., 70-73 beats per min) is adjusted (e.g., to 68-75 beats per min) to broaden the search.

The method would then continue to step 96 where the pattern search function to search within the expected ranges for heartbeat rate and respiration rate are adjusted. In this example, the signal would still not be found at step 98 until the expected ranges are adjusted to include a heartbeat rate of 80 beats per min. When the signals are found at step 98, the method continues with step 102 where the estimated respiration rate and heartbeat signal found within the expected ranges are output for display and/or further analysis.

FIG. 11B is a diagram of an example of human respiration and heart rate frequencies. Graph 104 depicts the respiration frequency signal and heart rate frequency signal for an infant. The respiration frequency signal is within the expected respiration rate range for an infant 106 and the heart rate frequency signal is within the expected heart rate range for an infant 108.

Graph 110 depicts the respiration frequency signal and heart rate frequency signal for a fit adult. The respiration frequency signal is within the expected respiration rate range for a fit adult 112 and the heart rate frequency signal is within the expected heart rate range for a fit adult 114.

The frequency ranges of the fit adult's respiration rate and heart rate are lower than that of the infant. In fact, the expected heart rate range for the fit adult 114 falls into the expected respiration rate range for the infant 106. For example, the expected respiration rate range for the infant 106 may be 30-60 breaths per minute while the expected heart rate range for the fit adult 114 may be between 40-60 beats per minute. Specifying the type of individual (e.g., fit adult or an infant) will help tune filtering for the pattern search function. Also, for an individual, heart rate will be higher in frequency and lower in amplitude than the respiration rate. These known qualities help to fine tune the pattern search function.

Figure 12:
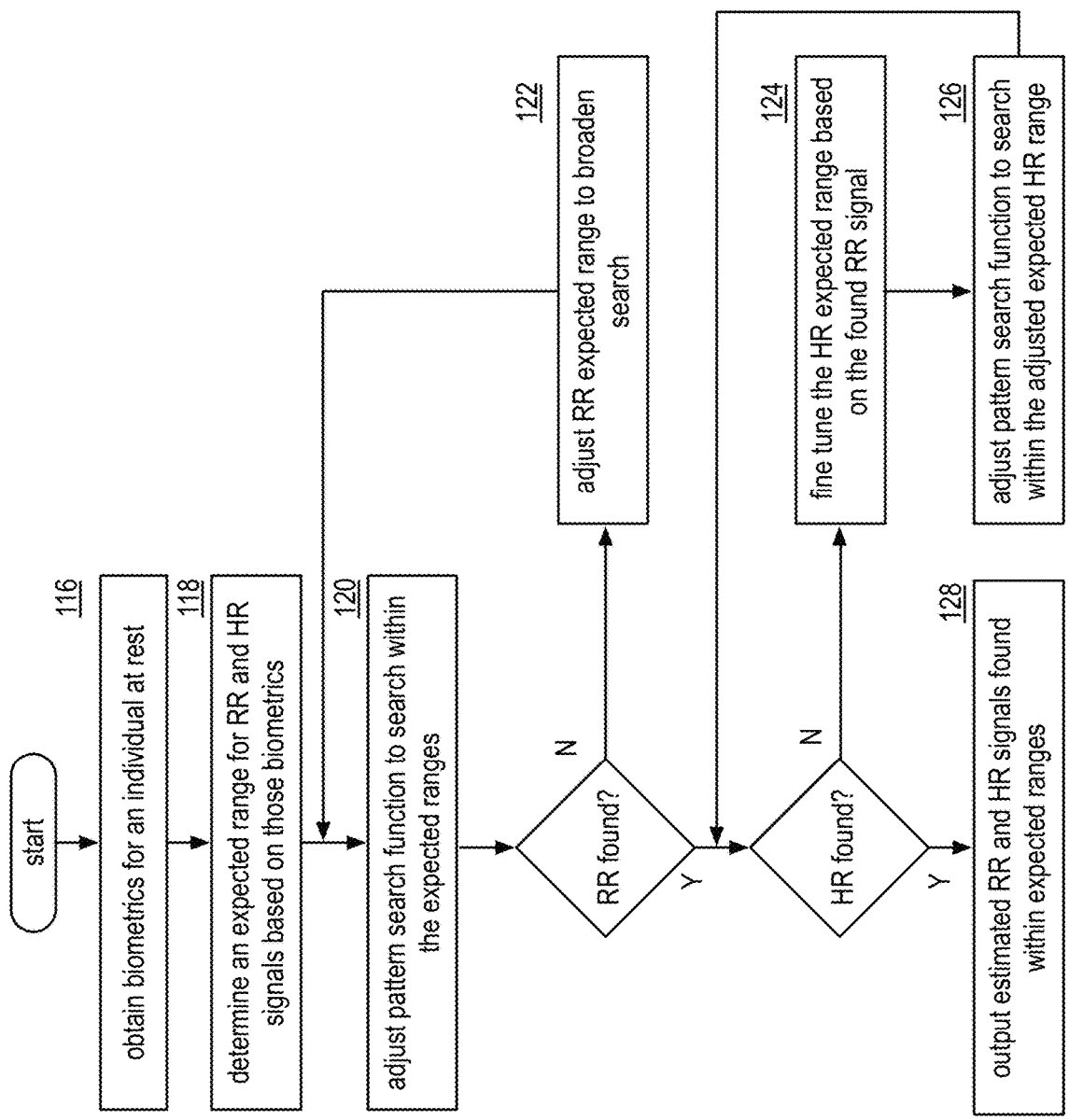
FIG. 12 is a flowchart illustrating another example of applying the repetitive bodily motion pattern search function in accordance with the present invention.

FIG. 12 is a flowchart illustrating another example of applying the repetitive bodily motion pattern search function. The method begins with step 116 where biometrics of an individual at rest are obtained. Biometrics of the individual may include age, sex, size, and physical condition (e.g., athlete, sedentary lifestyle, moderately active lifestyle, etc.).

The method continues with step 118 where the expected range for respiration rate and heart rate signals are determined based on the individual's biometrics. The method continues with step 120 where the pattern search function is adjusted to search within the expected ranges. If the respiration rate signal and heart rate signal are found within these expected ranges, the method continues to step 128 where the estimated respiration rate and heart rate are output for display and/or further analysis.

If the respiration rate is not found, the method continues to step 122 where the respiration rate range is adjusted to broaden the search range. The pattern search function would then be adjusted at step 120 to search within the updated expected ranges. If the respiration rate signal is detected but the heart rate signal is not found, the method continues to step 124 where the expected range for the heart rate is adjusted based on the found respiration signal. For example, the respiration rate is typically between ½ to ⅕ that of the heart rate. For instance, if the respiration rate is found to be 16 breaths per minute, the heart rate is most likely between 32 and 80 beats per minute. As such, with the respiration rate known, the range for the heart rate can be fine tuned to search within a range based on the respiration rate.

The method continues with step 126 where the pattern search function is adjusted within the adjusted expected heart rate signal range. Steps 124 and 126 repeat until the range is fine-tuned enough to discover the heart rate signal. When the heart rate signal is found, the method ends with step 128 where the estimated heart rate signal and the respiration rate signal are output for display and/or further analysis.

Figure 13:
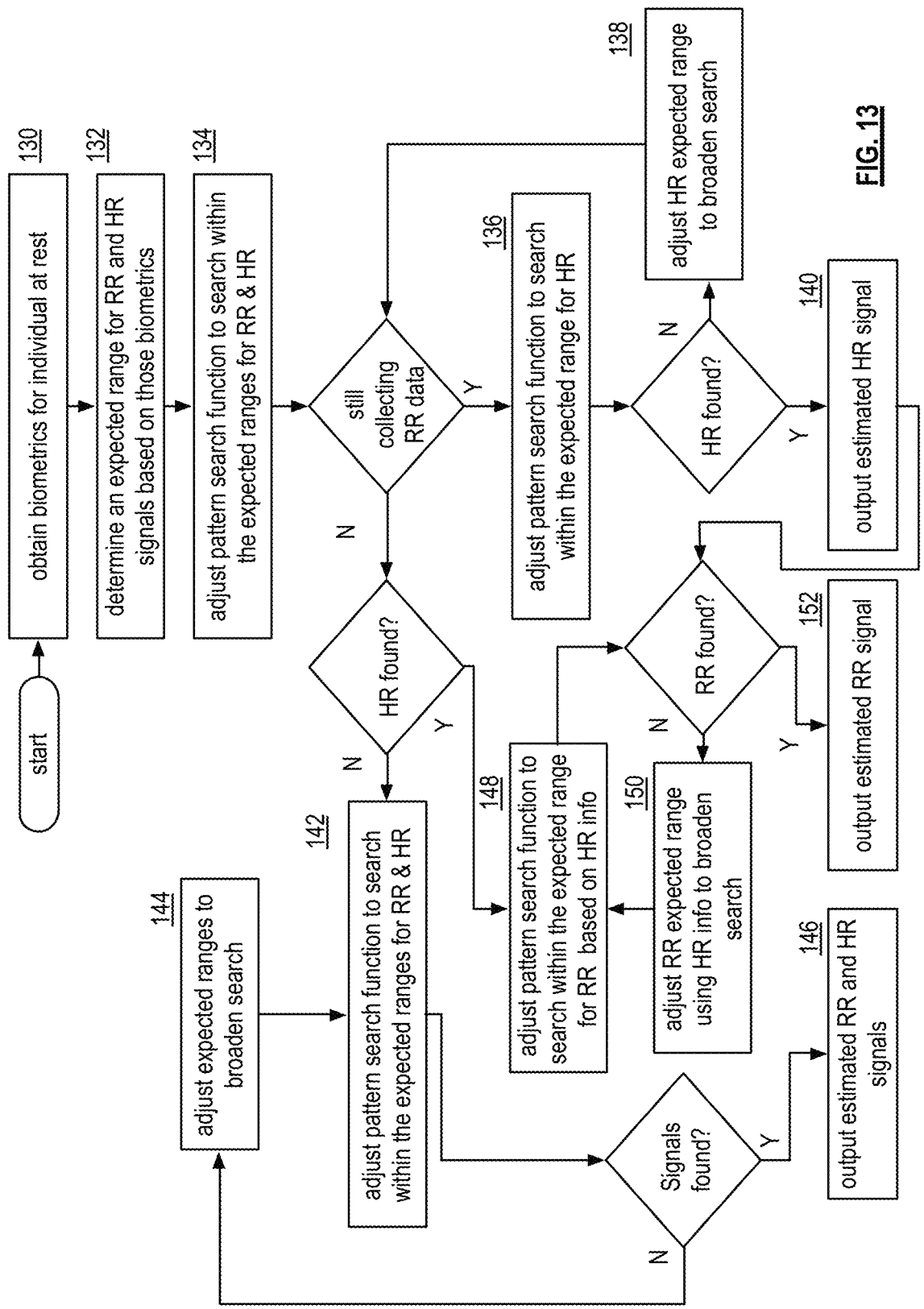
FIG. 13 is a flowchart illustrating another example of applying the repetitive bodily motion pattern search function in accordance with the present invention.

FIG. 13 is a flowchart illustrating another example of applying the repetitive bodily motion pattern search function. The method begins with step 130 where biometrics of an individual at rest are obtained. Biometrics of the individual may include age, sex, size, and physical condition (e.g., athlete, sedentary lifestyle, moderately active lifestyle, etc.).

The method continues with step 132 where the expected range for respiration rate and heart rate signals are determined based on the individual's biometrics. The method continues with step 134 where the pattern search function is adjusted to search within the expected ranges. If the respiration rate data is still being collected, the method continues to step 136 where the pattern search function is adjusted to search within the expected range for the heart rate. Because the frequency of respiration is less than that of the heart rate, it may take a longer amount of time to obtain the necessary respiration samples to estimate the respiration rate in comparison to the heart rate. Thus, time spent waiting for the respiration data to come in can be spent searching for and honing in on the heart rate signal.

If the heart rate is not found after step 136, the method continues to step 138 where the expected range for the heart rate is adjusted to broaden the search. The method returns to the step of checking whether the respiration data has been collected. If the respiration data is still being collected the method continues with step 136 where the pattern search function is adjusted to search within the new expected range for the heart rate. If the heart rate signal is found, the method continues with step 140 where the heart rate signal is output for display and/or further analysis. After the heart rate signal is found and output at step 140, the method branches to the step of determining whether the respiration rate has been found. At this point, the known heart rate data can be useful in determining the expected range of the respiration rate. The method would still be on hold here until the respiration data is collected.

If the respiration rate data has been collected, it is determined whether the heart rate has already been found. If the heart rate has not yet been found, the method continues with step 142 where the pattern search function is adjusted to search within the expected ranges for respiration rate and heart rate. If the signals are not found, the method continues to step 144 where the expected ranges for the respiration rate and heart rates are adjusted to broaden the search. When the signals are found, the method continues to step 146 where the estimated respiration rate and heart rate are output for display and/or further analysis.

If the heart rate has been found after the respiration rate data has been collected, the method continues to step 148 where the pattern search function is adjusted to search within the expected range for respiration rate based on the known heart rate information. For example, the respiration rate is typically between ½ to ⅕ that of the heart rate. For instance, if the heart rate is found to be 50 beats per minute, the respiration is most likely between 10 and 25 breaths per minute. As such, with the heart rate known, the range for the respiration rate can be adjusted to search within a range based on the respiration rate.

If the respiration rate is still not found, the method continues with step 150 where the expected respiration rate range is adjusted using the known heart rate information to further broaden the search. The method branches back to step 148 where the pattern search function is adjusted based on the new broadened parameters. When the respiration rate is found the method continues with step 152 where the estimated respiration rate is output for display and/or further analysis.

Figure 14:
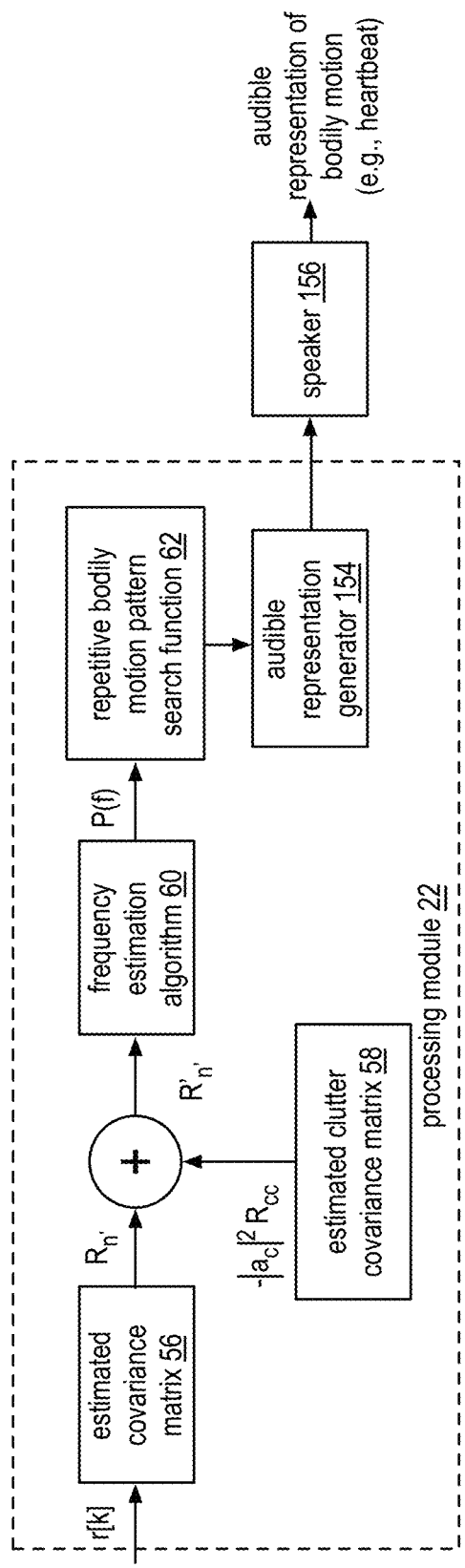
FIG. 14 is a schematic block diagram of an embodiment of a processing module of the wireless monitoring repetitive bodily movement system in accordance with the present invention.

FIG. 14 is a schematic block diagram of an embodiment of a processing module 22 of the computing device of the wireless monitoring repetitive bodily movement system. The processing module 22 includes an estimate covariance matrix module 56, an estimate clutter covariance matrix module 58, an adder, a frequency estimation algorithm module 60, a repetitive bodily motion pattern search function module 62, and an audible representation generator 154. The processing module 22 is coupled to a speaker 156. The speaker 156 may be a separate device or integrated into the computing device. Further, the speaker 156 may be a separate wireless device with Bluetooth connection capabilities.

The estimate covariance matrix module 56, estimate clutter covariance matrix module 58, adder, frequency estimation algorithm module 60, and repetitive bodily motion pattern search function module 62 operate as previously discussed in FIG. 22.

In an example of operation, the repetitive bodily motion pattern search function 62 sends the estimated repetitive bodily motion rate data to the audible representation generator 154. The audible representation generator 154 converts the data into an audible representation. For example, the audible representation generator 154 receives a signal representative of an estimated heart rate of an individual. The audible representation generator 154 converts the estimated heart rate signal into an audible representation of the heartbeat and sends it to the speaker 156 for output as sound.

As may also be used herein, the terms "processing module", "processing circuit", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

The present invention has been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of the various embodiments of the present invention. A module includes a processing module, a functional block, hardware, and/or software stored on memory for performing one or more functions as may be described herein. Note that, if the module is implemented via hardware, the hardware may operate independently and/or in conjunction software and/or firmware. As used herein, a module may contain one or more sub-modules, each of which may be one or more modules.

While particular combinations of various functions and features of the present invention have been expressly described herein, other combinations of these features and functions are likewise possible. The present invention is not limited by the particular examples disclosed herein and expressly incorporates these other combinations.

What is claimed is:

1. A method for determining a rate of repetitive bodily motion of an individual without requiring contact with the individual, wherein the method is executable by one or more computing devices and comprises:
    transmitting a signal for reflection off of the individual;
    receiving a reflected signal;
    applying a frequency estimation algorithm to the reflected signal to produce an estimated spectral density, wherein the estimated spectral density is in frequency domain and includes at least one frequency component corresponding to the repetitive bodily motion, and wherein the applying the frequency estimation algorithm includes:
        estimating a covariance matrix of the reflected signal;
        estimating a clutter covariance matrix of the reflected signal;
        generating a resultant matrix from the clutter covariance matrix and the covariance matrix; and
        applying the frequency estimation algorithm to the resultant matrix to produce the estimated spectral density; and
    applying a repetitive bodily motion pattern search function to the estimated spectral density to estimate the rate of the repetitive bodily motion of the individual based on the at least one frequency component.

2. The method of claim 1 further comprises:
    the transmitting the signal for reflection off of the individual is performed by a first computing device of the one or more computing devices;
    the receiving the reflected signal is performed by the first computing device of the one or more computing devices;
    the applying the frequency estimation algorithm to the reflected signal to produce the estimated spectral density is performed by a second computing device of the one or more computing devices; and
    the applying the repetitive bodily motion pattern search function to the estimated spectral density is performed by the second computing device of the one or more computing devices.

3. The method of claim 1, wherein the transmitting the signal comprises:

generating a continuous wave reference signal;
up-converting the continuous wave reference signal to a radio frequency signal; and
transmitting the radio frequency signal as the signal.

4. The method of claim 1, wherein the reflected signal comprises one or more of:
the transmitted signal;
a clutter signal;
a multipath signal;
a noise component; and
a Doppler shifted version of the repetitive bodily motion.

5. The method of claim 1, wherein the repetitive bodily motion comprises at least one of:
heartbeat;
respiration;
eye movement;
spasms; and
ticks.

6. The method of claim 1, wherein the frequency estimation algorithm is a multiple signal classification (MUSIC) algorithm.

7. The method of claim 1, wherein the applying the repetitive bodily motion pattern search function comprises:
applying a heartbeat and respiration search function to the estimated spectral density to determine principal frequency components of heartbeat and respiration, wherein the heartbeat and the respiration correspond to the repetitive bodily motion; and
estimating a heart rate and a respiration rate from the determined principal frequency components.

8. The method of claim 7 further comprises:
determining characteristics of the individual; and
selecting the heartbeat and respiration search function from a plurality of heartbeat and respiration search functions based on the characteristics of the individual.

9. The method of claim 1, wherein the applying the repetitive bodily motion pattern search function comprises:
applying an eye movement search function to the estimated spectral density to determine principal frequency components of eye movement, wherein the eye movement corresponds to the repetitive bodily motion; and
estimating an eye movement rate from the determined principal frequency components.

10. The method of claim 1 further comprises:
outputting the rate of the repetitive bodily motion.

11. The method of claim 1 further comprises:
applying the repetitive bodily motion pattern search function to the estimated spectral density to generate an audible representation of the repetitive bodily motion of the individual.

12. The method of claim 1 further comprises:
down-converting the reflected signal to a baseband signal; and
applying the frequency estimation algorithm to the baseband signal to produce the estimated spectral density.

13. A computing device comprises:
a transceiver operable to:
transmit a signal for reflection off of an individual;
receive a reflected signal; and
a memory; and
a processing module operably coupled to the transceiver and the memory, wherein the processing module is operable to:
apply a frequency estimation algorithm to the reflected signal to produce an estimated spectral density, wherein the estimated spectral density is in frequency domain includes at least one frequency component corresponding to the repetitive bodily motion, and wherein the processing module is operable to apply the frequency estimation algorithm by:
estimating a covariance matrix of the reflected signal;
estimating a clutter covariance matrix of the reflected signal;
generating a resultant matrix from the clutter covariance matrix and the covariance matrix; and
applying the frequency estimation algorithm to the resultant matrix to produce the estimated spectral density; and
apply a repetitive bodily motion pattern search function to the estimated spectral density to estimate the rate of the repetitive bodily motion of the individual based on the at least one frequency component.

14. The computing device of claim 13, wherein the transceiver further functions to transmit the signal by:
generating a continuous wave reference signal;
up-converting the continuous wave reference signal to a radio frequency signal; and
transmitting the radio frequency signal as the signal.

15. The computing device of claim 13, wherein the reflected signal comprises one or more of:
the transmitted signal;
a clutter signal;
a multipath signal;
a noise component; and
a Doppler shifted version of the repetitive bodily motion.

16. The computing device of claim 13, wherein the repetitive bodily motion comprises at least one of:
heartbeat;
respiration;
eye movement;
spasms; and
ticks.

17. The computing device of claim 13, wherein the frequency estimation algorithm is a multiple signal classification (MUSIC) algorithm.

18. The computing device of claim 13, wherein the processing module further functions to apply the repetitive bodily motion pattern search function by:
applying a heartbeat and respiration search function to the estimated spectral density to determine principal frequency components of heartbeat and respiration, wherein the heartbeat and the respiration correspond to the repetitive bodily motion; and
estimating a heart rate and a respiration rate from the determined principal frequency components.

19. The computing device of claim 18, wherein the processing module is further operable to:
determine characteristics of the individual; and
select the heartbeat and respiration search function from a plurality of heartbeat and respiration search functions based on the characteristics of the individual.

20. The computing device of claim 13, wherein the processing module further functions to apply the repetitive bodily motion pattern search function by:
applying an eye movement search function to the estimated spectral density to determine principal frequency components of eye movement, wherein the eye movement corresponds to the repetitive bodily motion; and
estimating an eye movement rate from the determined principal frequency components.

21. The computing device of claim 13, wherein the processing module is further operable to:
output the rate of the repetitive bodily motion.

22. The computing device of claim 13, wherein the processing module is further operable to:
    apply the repetitive bodily motion pattern search function to the estimated spectral density to generate an audible representation of the repetitive bodily motion of the individual.

23. The computing device of claim 13, further comprises:
    the transceiver is further operable to down-convert the reflected signal to a baseband signal; and
    the processing module is further operable to apply the frequency estimation algorithm to the baseband signal to produce the estimated spectral density.

\* \* \* \* \*